(12) United States Patent
Guse, III

(10) Patent No.: US 10,751,231 B2
(45) Date of Patent: Aug. 25, 2020

(54) SYSTEM FOR POWERING MEDICAL IMAGING SYSTEMS

(71) Applicant: Lifeline Mobile, Inc., Columbus, OH (US)

(72) Inventor: Kenneth L Guse, III, Pickerington, OH (US)

(73) Assignee: Lifeline Mobile, Inc., Columbus, OH (US)

( * ) Notice: Subject to any disclaimer, the term of this patent is extended or adjusted under 35 U.S.C. 154(b) by 623 days.

(21) Appl. No.: 15/611,376

(22) Filed: Jun. 1, 2017

(65) Prior Publication Data

US 2018/0344271 A1    Dec. 6, 2018

(51) Int. Cl.
*A61G 3/00* (2006.01)
*A61B 6/00* (2006.01)
*A61B 1/00* (2006.01)

(52) U.S. Cl.
CPC ............ *A61G 3/001* (2013.01); *A61B 6/4405* (2013.01); *A61B 6/56* (2013.01); *A61B 1/00027* (2013.01); *A61B 6/502* (2013.01)

(58) Field of Classification Search
CPC ..................................................... A61G 3/001
See application file for complete search history.

(56) References Cited

U.S. PATENT DOCUMENTS

| 4,053,778 A | 10/1977 | Franke |
| 4,186,329 A | 1/1980 | Fairbairn |
| 4,797,907 A | 1/1989 | Anderton |
| 5,272,612 A | 12/1993 | Harada et al. |
| RE35,025 E | 8/1995 | Anderton |
| 5,448,443 A | 9/1995 | Muelleman |
| 5,530,362 A | 6/1996 | Boehm et al. |
| 5,666,255 A | 9/1997 | Muelleman |

(Continued)

OTHER PUBLICATIONS

N. Mutoh and T. Inoue, "A Control Method to Charge Series-Connected Ultraelectric Double-Layer Capacitors Suitable for Photovoltaic Generation Systems Combining MPPT Control Method," in IEEE Transactions on Industrial Electronics, vol. 54, No. 1, pp. 374-383, Feb. 2007. (Year: 2007).*

(Continued)

*Primary Examiner* — Daniel J Cavallari
(74) *Attorney, Agent, or Firm* — Standley Law Group LLP; Jeffrey S. Standley; Adam J. Smith

(57) ABSTRACT

Disclosed herein is a system and method for powering a medical imaging machine as well as an accompanying workstation, the system comprising an engine connected to a generator with a main circuit panel in electrical connection with the generator to create a branch circuit. Embodiments include a DC power supply electrically connected to the branch circuit; an inverter placed in electrical connection with a plurality of capacitors electrically connected in series; a generator control in electronical connection with the inverter and the generator; and an inverter panel in electrical communication with the inverter and providing a first output at a first voltage for the medical imaging machine and a second output at a second voltage for the workstation controls of the medical imaging machine. In a preferred embodiment, the engine is further arranged for propelling a truck which contains all of the power system components along with the medical imaging system.

13 Claims, 4 Drawing Sheets

(56) References Cited

U.S. PATENT DOCUMENTS

| | | |
|---|---|---|
| 5,781,386 A | 7/1998 | Meulleman |
| 5,867,561 A | 2/1999 | Strasser et al. |
| 6,169,782 B1 | 1/2001 | Zetterlund |
| 6,205,200 B1 | 3/2001 | Boyer et al. |
| 6,563,717 B2 | 5/2003 | Lunding et al. |
| 6,624,997 B1 | 9/2003 | Llanos et al. |
| 7,050,539 B2 | 5/2006 | Loef et al. |
| 7,356,121 B2 | 4/2008 | Schwarz |
| 9,337,901 B2 | 5/2016 | Takahashi |
| 2005/0281377 A1 | 12/2005 | Heinze |
| 2007/0253540 A1 | 11/2007 | Anderton et al. |
| 2008/0157594 A1* | 7/2008 | Peterson .................. H02P 9/48 307/10.1 |
| 2010/0301985 A1 | 12/2010 | Luo et al. |
| 2012/0256099 A1 | 10/2012 | Gregerson et al. |
| 2013/0223596 A1 | 8/2013 | Kojima et al. |
| 2017/0027537 A1 | 2/2017 | Zhang et al. |
| 2017/0231843 A1* | 8/2017 | Thompson ............. A61B 6/032 378/20 |

OTHER PUBLICATIONS

Controlled Power Company, http://www.controlledpwr.com/Medical_Power_Products.html, webpage, Mar. 22, 2017, 1 page.
Teal, Medical Imaging, https://www.mtecorp.com/industries/medical-imaging/, webpage, Mar. 22, 2017, 1 page.
Powervar, Medical Power Conditioners, brochure, Mar. 22, 2017, 2 pages.
Russel, Michael, Medical Imaging Systems Need Special Care, Too, magazine article, Mar./Apr. 1991, 7 pages.
SCE&G a SCANA Company, Power Quality for Diagnostic Medical Imaging Systems, catalog, Mar. 22, 2017, 53 pages.
Controlled Power Company, SureImage Imaging and Treatment Series, brochure, Mar. 22, 2017, 8 pages.
Teal, https://www.mtecorp.com/products/power-management/, Power Management webpage, Mar. 22, 2017, 1 page.

* cited by examiner

SYSTEM FOR POWERING MEDICAL IMAGING SYSTEMS

CROSS-REFERENCE TO RELATED APPLICATIONS

This application does not claim priority to any co-pending applications.

TECHNICAL FIELD

Embodiments generally relate to systems for powering medical imaging systems, including but not limited to mammography systems.

BACKGROUND OF THE ART

Mobile medical clinics have been seen as a way to provide medical care to underserved portions of the population or in rural areas where building a traditional medical office would be cost prohibitive. Generally speaking, these mobile medical clinics provide either a frame on wheels that is powered by a traditional commercial truck motor or a trailer with wheels that is pulled by a traditional semi or tractor-trailer. However, since traditional power from the grid is not always available, power must be generated on site. This can pose a significant problem for medical imaging systems, which require a power source that is both strong and clean (free of voltage dips, spikes, transients, etc.) in order to provide a regulated dose of radiation.

Similarly, hospitals and other medical care facilities often have backup or redundant power systems, such as generators, to provide power when traditional power from the grid is not available. Such systems may be used, for example without limitation, in the event of a natural disaster, power outage, or other emergency situation. This can likewise pose a significant problem for medical imaging systems, which require a power source that is both strong and clean (free of voltage dips, spikes, transients, etc.) in order to provide a regulated dose of radiation.

SUMMARY OF THE EXEMPLARY EMBODIMENTS

Exemplary embodiments provide a system which generates clean power for use with medical imaging systems. The power can be generated by an engine for operating a truck on which the medical imaging system has been placed, or could be generated by a separate engine. No traditional UPS is necessary to clean the power sent to the medical imaging system. A bank of capacitors may be placed in series and in electrical connection with both a power supply and inverter.

The foregoing and other features and advantages of the present invention will be apparent from the following more detailed description of the particular embodiments, as illustrated in the accompanying drawings.

BRIEF DESCRIPTION OF THE DRAWINGS

A better understanding of an exemplary embodiment will be obtained from a reading of the following detailed description and the accompanying drawings wherein identical reference characters refer to identical parts and in which.

DETAILED DESCRIPTION

Figure 1:
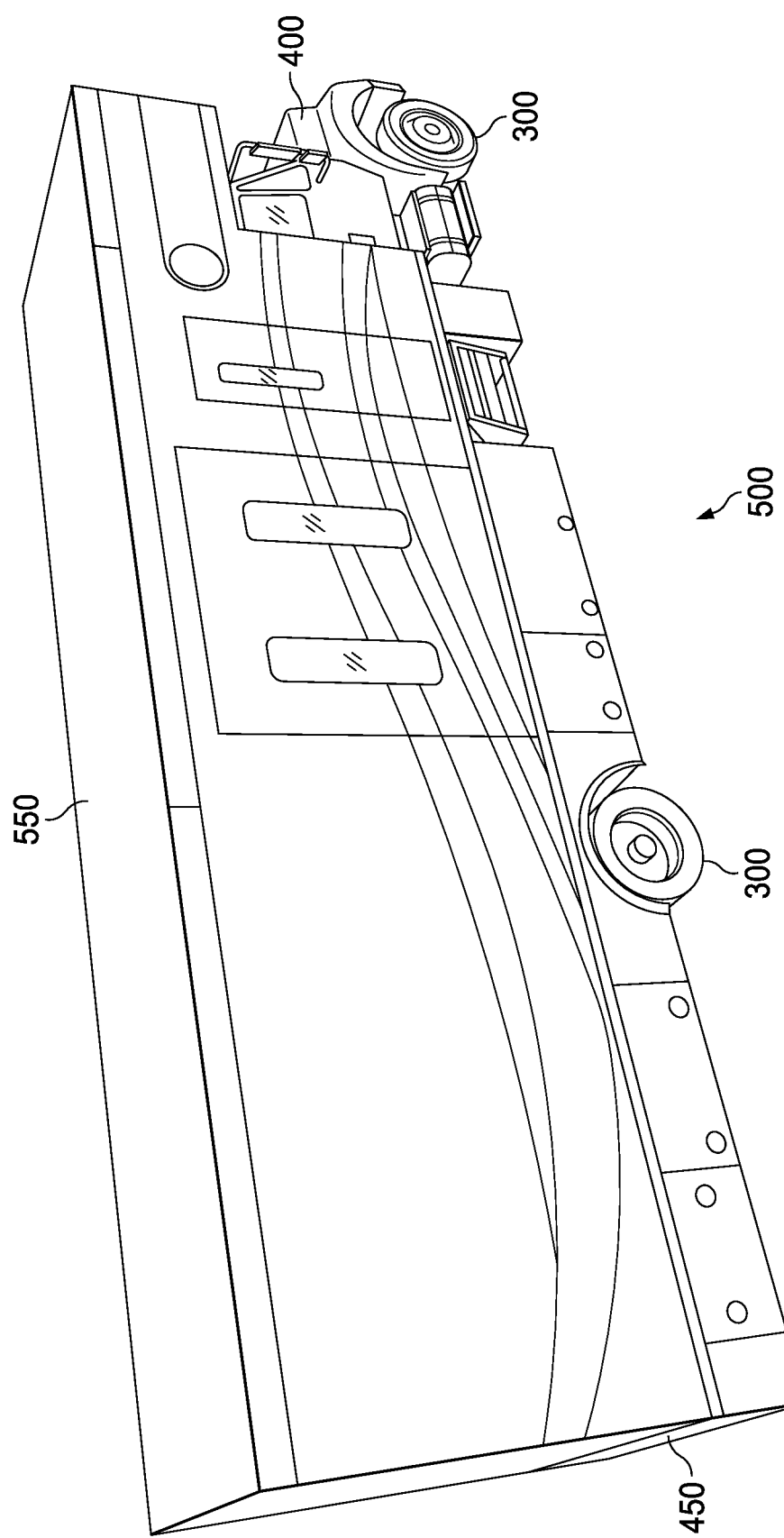
FIG. 1 is a perspective illustration of one type of mobile medical clinic, where the structure is built upon a traditional industrial truck frame with an engine that is fixed relative to the frame.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a perspective illustration of one type of mobile medical clinic 500, where the structure is built upon a vehicle with an engine 400 that is fixed relative to the chassis 450. A set of wheels 300 allow the mobile medical clinic 500 to travel from location to location, similar to any normal recreational or passenger hauling vehicle. An enclosure 550 is provided atop the chassis 450, in order to house most of the necessary equipment, including but not limited to desks/tables, computers, various types of medical imaging equipment, exam tables, and other medical/office related items for operating a mobile medical clinic 500.

Figure 2:
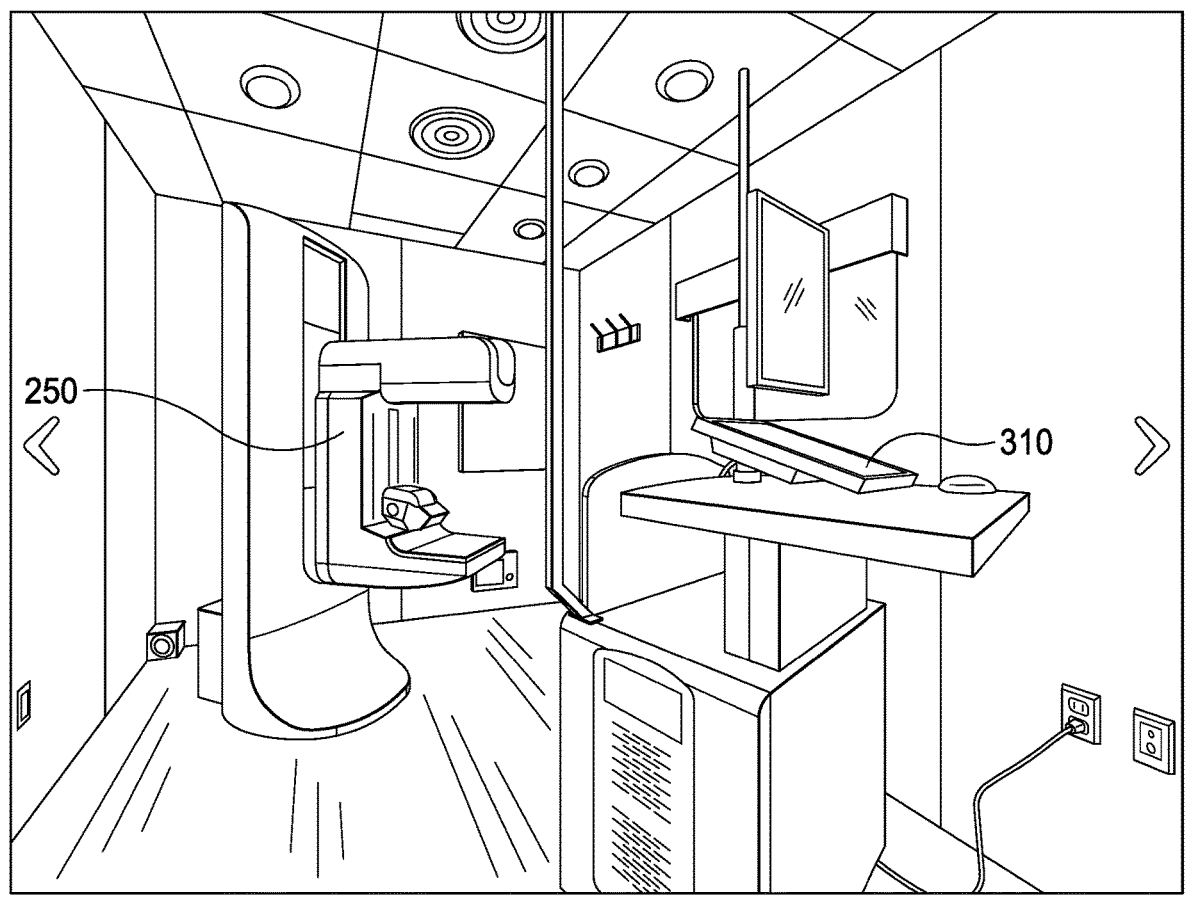
FIG. 2 is a perspective illustration of the interior of the mobile medical clinic shown in FIG. 1.

FIG. 2 is a perspective illustration of the interior of the enclosure 550 of the mobile medical clinic 500. Here we see a medical imaging machine 250 placed within the enclosure 550, along with a user workstation 310 for operating the medical imaging machine 250. While the medical imaging machine 250 is often a mammography machine, any other medical image device could be used, including but not limited to general X-ray, CT scans, magnetic resonance imaging (MRI), ultrasounds, endoscopy, elastography, tactile imaging, thermography, medical photography and nuclear medicine functional imaging techniques such as positron emission tomography (PET) and Single-photon emission computed tomography (SPECT). In exemplary embodiments, the medical imaging machine 250 is transportable, though such is not required. The illustrated interior is merely exemplary and is not intended to be limiting.

Figure 3:
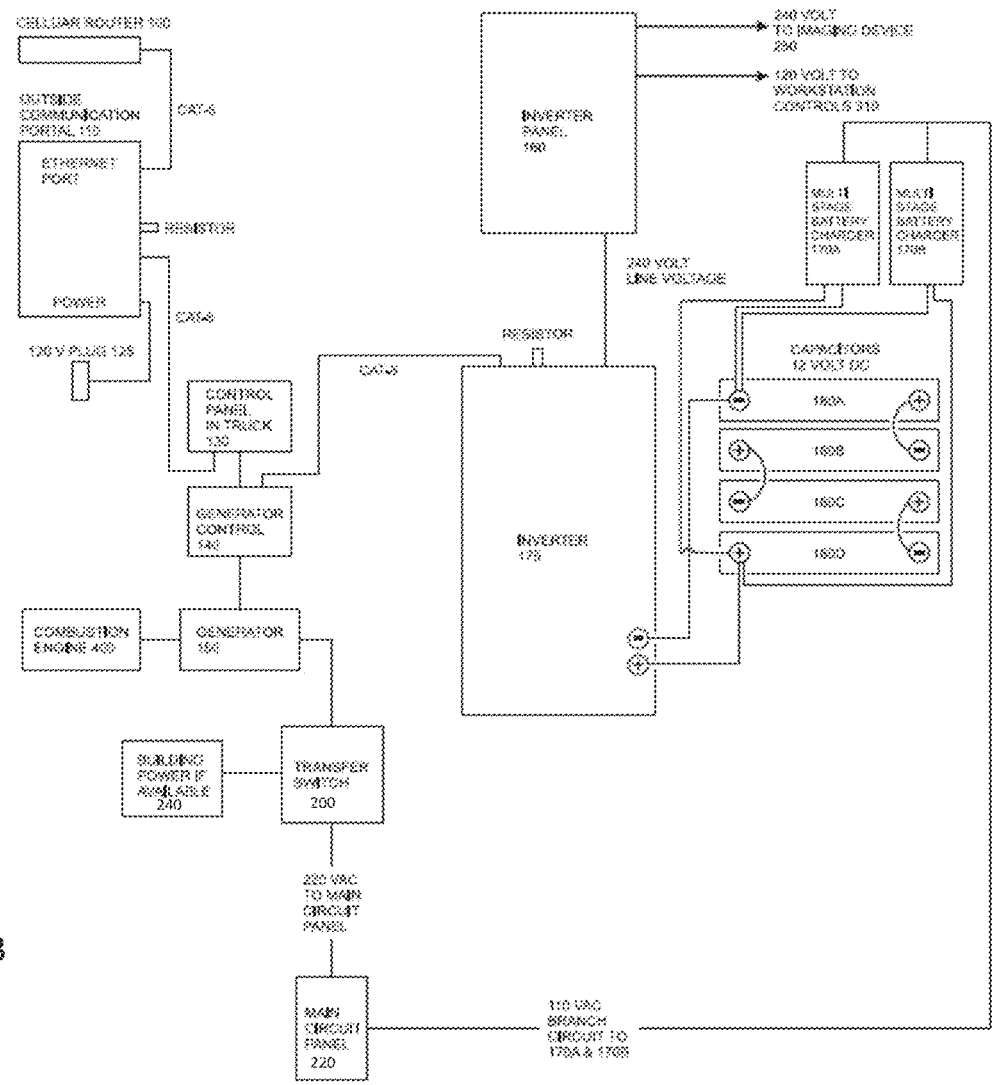
FIG. 3 is an electrical block diagram for an exemplary embodiment of the power system.

FIG. 3 is an electrical block diagram for an exemplary embodiment of the power system. The combustion engine 400 of the mobile medical clinic 500 may be used in combination with the generator 150 in order to create power for the system. In some embodiments, however, a different combustion engine may be used to create power for the system, for example a secondary combustion engine specifically for the generator 150. Furthermore, while reference is made herein to the mobile medical clinic 500 and associated engine 400 and generator 150, it is contemplated that any of the embodiments shown or described herein may be used in any application or context. For example, but not to serve as a limitation, the present invention may be utilized with backup or redundant generator power systems for a hospital or other medical care facility.

The generator 150 may supply power to a transfer switch 200, which can optionally be in electrical connection with building power 240, if available, so that the switch 200 would control whether power from the generator 150 or the building 240 would be sent through the system. The switch 200 is preferably in electrical connection with a main circuit panel 220 which is then placed in electrical connection with a first and second DC power supplies 170A and 170B.

A generator control 140 is preferably in electrical connection with the generator 150 in order to control operations of the generator 150. The generator control 140 may be used to start the generator 150 if grid power is lost unexpectedly to protect the imaging equipment, though such is not required.

A control panel 130 for the mobile medical clinic 500 may be in electrical connection with the generator controls 140 as well as an outside communication portal 110, which can receive outside electrical communications from either an Ethernet port or from a cellular router 100, though any type of network connectivity device is contemplated. These communications are generally low voltage and provide electrical communication between the components, power would generally be provided in addition to the electrical communication instructions. As shown, CAT 5 cable is preferable for connecting these components, although this is not required. In this way, the control panel 130 may be in communication with a remote electronic device, such as but not limited to, a computer. This connection may enable remote access to the control panel 130 and components in connectivity therewith for diagnostic review of the system, notification of actual or potential errors, remote updates, remote changes to setting, and the like.

An inverter 175 is preferably placed in direct electrical connection with a bank of capacitors 180A-180D which are arranged in series with one another. Thus, a first capacitor 180A is connected in series to a second capacitor 180B, which is in turn connected in series to a third capacitor 180C, which is in turn connected to a fourth capacitor 180D. It should be noted, that although four capacitors are shown, this is not a requirement of the invention, which could be practiced with any number of capacitors that is appropriate for the application. The bank of capacitors 180A-180D may be wired to supply DC voltage to the input side of the inverter 175 so that the inverter 175 output is appropriately sized for the load of the medical imaging machine 250. It should be appreciated that while a single inverter 175 may be discussed, it is contemplated that multiple inverters 175 may be utilized in the same location or at various location in the power system.

In this embodiment, a negative conduction line connects directly between the inverter 175 and the negative post on the first capacitor 180A. Preferably, a positive conduction line connects directly between the inverter 175 and the positive terminal on the last capacitor 180D. The first and second DC Power Supplies 170A and 170B each contain a positive and negative conduction line where both positive lines connect to the positive terminal on the inverter 175 and both negative lines connect to the negative terminal on the inverter 175. These DC power supplies 170A and 170B keep the bank of capacitor 180A-180D charged and provide extra power to handle spikes in voltage demand from the input side of the inverter 175 when medical imaging machine 250 is in use. Such consistent power is generally required to provide a proper dose of radiation from the medical imaging machine 250.

The inverter 175 is preferably then placed in electrical connection with the inverter panel 160, which preferably provides a first output at a first voltage to the imaging machine 250 and a second output at a second voltage to the workstation controls 310. In this particular embodiment, the output to the imaging machine 250 is provided as 240V while the output for the workstation controls 310 is provided as 120V, but this is not required as other voltage combinations could be delivered as well.

An exemplary inverter 175 is a Conext XW 6848, though any type of inverter 175 is contemplated. An exemplary capacitor for use with the bank of capacitors 180A-180D is a Maxwell BMOD0500 P016 B01 16V Ultracapacitor, though any type of capacitor is contemplated. The DC power supplies 170A and 170B may be multi stage battery chargers, though such is not required. An exemplary DC power supply for use with the first and second DC power supplies 170A and 170B is a PowerMax PM3-48V Series Battery Charger, though any type of DC power supply is contemplated. In exemplary embodiment where the PowerMax PM3-48V Series Battery Charger is used, it may be modified to produce a constant 62 VDC or to otherwise work with the devices, systems, and methods described herein.

As noted above, in a traditional system, the necessary power is generated by a generator and then sent to the imaging machine, however, it has been found that this power can be "dirty" or have voltage spikes, voltage sags, or general artifacts in the sine wave which can affect sensitive electronics in the imaging machine. Prior attempts to solve this issue have used uninterruptible power supplies (UPS) for the imaging machine. However, these UPS devices can be expensive, heavy, and require a large volume of space in the mobile medical clinic.

As shown in the embodiments above, after generating the power, the system can "clean" the power by using the capacitors 180A-180D, without requiring the expense, weight, and space necessary for a traditional UPS device. It has been discovered, that this arrangement allows a much smaller generator 150 to be used, which further reduces the weight and space required for the power system. In one experiment, the generator size was reduced from a 40,000 Watt generator down to a 20,000 Watt generator. What was also discovered and was not anticipated, was that "wet-stacking" of the generator engine could also be reduced. Thus, when using a 40,000 Watt generator with a traditional UPS device, it was common to observe wet-stacking because the size of the generator was much larger than the amount of power that was actually necessary for the medical imaging machine. This caused the generator engine to run on a light load for an extended period of time, which can cause unburnt fuel to deposit within the engine or its exhaust system, i.e. wet-stacking. However, with the system disclosed herein, wet-stacking was effectively eliminated by using a smaller generator with an engine that is running for extended periods of time at a medium or high load, as opposed to the low loads which can cause wet-stacking.

Figure 4:
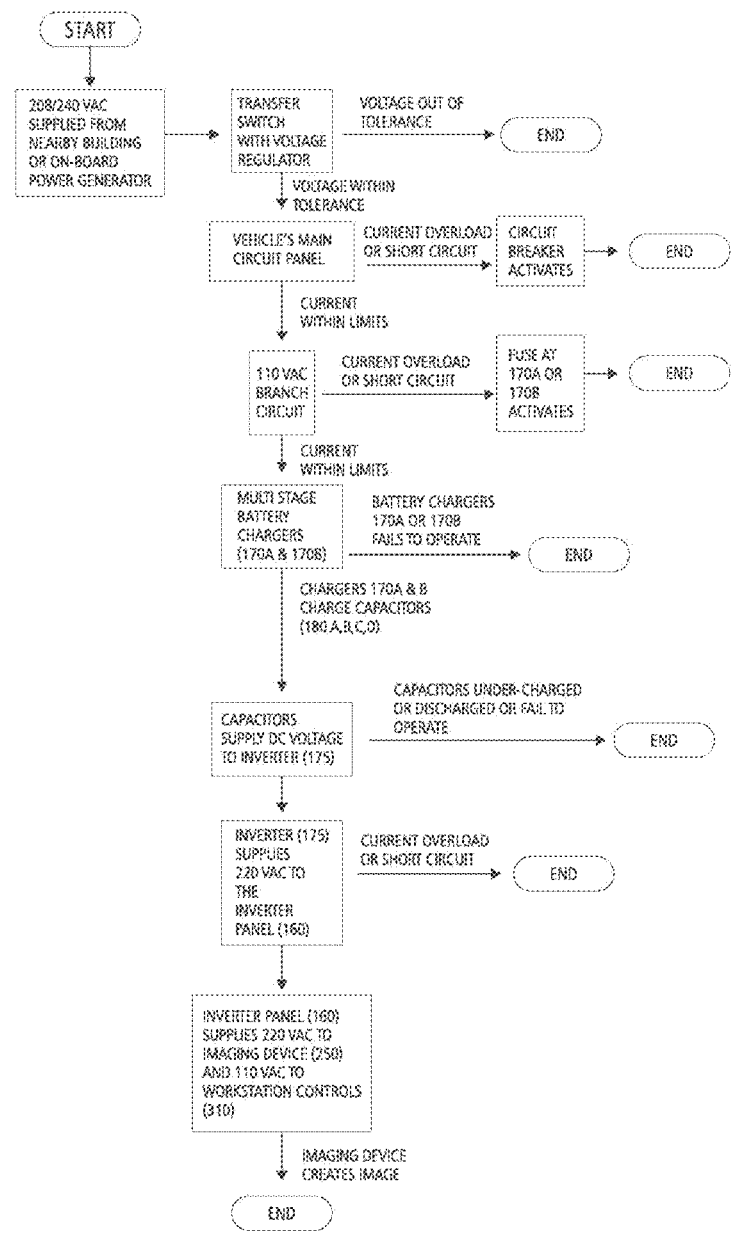
FIG. 4 is a logic flow chart of one embodiment for operating the system shown in FIG. 3.

FIG. 4 is a logic flow chart of one embodiment for operating the system shown in FIG. 3. Either the generator 150, or a nearby building 240, should preferably provide 208/240 VAC to the switch 200. If the voltage applied to the switch 200 is outside of tolerance, the system is shut down. This power is then preferably transmitted to the main circuit panel 220, which contains various circuit breakers, which will open in the case of a short circuit or overload of the circuit. If the current is within prescribed limits, this power would then be sent to the DC power supplies 170A/170B though the 110 VAC branch circuit. If a current overload or short circuit were to occur at this position, the DC power supplies 170A/170B contain fuses, which would open similar to the circuit breakers on the main circuit panel 220 described above.

The DC power supplies 170A/170B preferably charge the capacitors 180A-D, and supply DC voltage to the inverter 175. If capacitors 180A-D are undercharged, or discharged, or fail to operate, the system is shut down. The inverter 175 preferably supplies 220 VAC to the inverter panel 160, which preferably supplies 220 VAC to the imaging device 250 while supplying 110 VAC to the workstation 310. This power would then be used in each device 250/310 to generate the medical image.

Having shown and described a preferred embodiment of the invention, those skilled in the art will realize that many variations and modifications may be made to affect the described invention and still be within the scope of the claimed invention. Additionally, many of the elements indicated above may be altered or replaced by different elements which will provide the same result and fall within the spirit of the claimed invention. It is the intention, therefore, to limit the invention only as indicated by the scope of the claims.

What is claimed is:

1. A system for powering a medical imaging machine as well as an accompanying workstation, the system comprising:
an engine connected to a generator;
a main circuit panel in electrical connection with the generator to create a branch circuit;
a DC power supply electrically connected to the branch circuit;
an inverter placed in electrical connection with a plurality of capacitors electrically connected in series, where a first capacitor is in direct electrical connection with the inverter and with the DC power supply, and where a last capacitor is in direct electrical connection with the inverter and with the DC power supply;
a generator control in electrical connection with the inverter and the generator; and
an inverter panel in electrical communication with the inverter and providing a first output at a first voltage for the medical imaging machine and a second output at a second voltage for the workstation controls of the medical imaging machine.

2. The system of claim 1 wherein:
the inverter panel accepts power from the inverter at 240V, and creates a 240V output for the medical imaging machine along with a 120V output for workstation controls.

3. The system of claim 1 wherein:
no uninterruptible power supply is placed between the generator and the medical imaging machine.

4. The system of claim 1 wherein:
the generator control sends low voltage electrical communication signals to the generator; and
the generator sends high voltage electrical power to the inverter.

5. The system of claim 1 wherein:
the inverter is connected to a negative conduction line which is in direct electrical connection with the first capacitor; and
the inverter is connected to a positive conduction line which is in direct electrical connection with the last capacitor.

6. The system of claim 1 wherein:
the engine is a combustion engine used to move the medical imaging machine.

7. The system of claim 1 wherein:
the capacitors are supplied with an appropriate voltage of DC power.

8. The system of claim 1 further comprising:
a frame supported by wheels which is fixed relative to the generator.

9. The system of claim 1 further comprising:
a control panel in electrical connection with the generator control; and
an outside communication portal in electrical connection with the control panel.

10. The system of claim 9 wherein:
the outside communication portal includes an Ethernet port which is in electrical connection with a cellular router.

11. A system for powering a medical imaging machine comprising:
an engine connected to a generator as well as arranged to propel the frame of a truck;
a DC power supply electrically connected to the generator;
a plurality of capacitors electrically connected in series with one another, where a first capacitor is in electrical connection with the inverter and the DC power supply and a last capacitor is in electrical connection with the inverter and the DC power supply;
an inverter placed in electrical connection with the first capacitor and the last capacitor;
a generator control in electrical communication with the inverter and the generator; and
an inverter panel in electrical connection with the inverter and providing an output at a first voltage for the medical imaging machine.

12. The system of claim 11 wherein:
the inverter panel also provides a second output at a second voltage for workstation controls of the medical imaging machine.

13. The system of claim 12 wherein:
the first voltage is approximately 240 Volts while the second voltage is approximately 120 Volts.

* * * * *